United States Patent
Wahl et al.

(10) Patent No.: US 11,246,720 B2
(45) Date of Patent: Feb. 15, 2022

(54) PROSTHETIC ELBOW WITH ADJUSTABLE COUNTERBALANCE MECHANISM

(71) Applicant: Hugh Steeper Limited, Leeds (GB)

(72) Inventors: Ryan Wahl, Richmond, MI (US); Aaron Taszreak, China, MI (US)

(73) Assignee: Hugh Steeper Limited, Leeds (GB)

( * ) Notice: Subject to any disclaimer, the term of this patent is extended or adjusted under 35 U.S.C. 154(b) by 125 days.

(21) Appl. No.: 16/696,807

(22) Filed: Nov. 26, 2019

(65) Prior Publication Data

US 2021/0154026 A1 May 27, 2021

(51) Int. Cl.
*A61F 2/58* (2006.01)
*A61F 2/68* (2006.01)
*A61F 2/50* (2006.01)
*A61F 2/54* (2006.01)

(52) U.S. Cl.
CPC ........ *A61F 2/582* (2013.01); *A61F 2002/503* (2013.01); *A61F 2002/5039* (2013.01); *A61F 2002/5078* (2013.01); *A61F 2002/543* (2013.01); *A61F 2002/6836* (2013.01)

(58) Field of Classification Search
CPC .... A61F 2/56; A61F 2/58; A61F 2/582; A61F 2002/5078
See application file for complete search history.

(56) References Cited

U.S. PATENT DOCUMENTS

| | | | |
|---|---|---|---|
| 2,537,551 A * | 1/1951 | Sansbury | A61F 2/58 623/57 |
| 2,626,398 A * | 1/1953 | Grindle | A61F 2/582 623/59 |
| 2,800,345 A | 7/1957 | Goodwin et al. | |
| 3,107,358 A | 10/1963 | Prout | |
| 4,038,706 A | 8/1977 | Ober et al. | |
| 4,067,070 A | 1/1978 | Seamone et al. | |
| 5,888,235 A | 3/1999 | Jacobsen et al. | |
| 7,935,153 B2 | 5/2011 | Auberger | |
| 8,900,327 B2 | 12/2014 | Bertels et al. | |

* cited by examiner

*Primary Examiner* — Marcia L Watkins
(74) *Attorney, Agent, or Firm* — Rahman LLC (57) ABSTRACT

An adjustable counterbalance mechanism for a prosthetic elbow includes a torsional spring disposed in a housing structure coaxially to an axis of rotation of a forearm portion and a cord and pulley arrangement which includes a first pulley, a second pulley and a link member attached to a fixed member structure. The first pulley is attached to a second portion of the spring and connected to the second pulley by a first cord. The second pulley is pivotally attached to the housing structure and connected to the link member by a second cord. The cord and pulley arrangement is configured to transfer a moment of force due to spring force to the forearm portion to counteract the torque of a forearm due to gravity as the angle of the forearm portion changes relative to the upper arm portion.

10 Claims, 8 Drawing Sheets

PROSTHETIC ELBOW WITH ADJUSTABLE COUNTERBALANCE MECHANISM

FIELD OF THE INVENTION

The invention relates to a prosthetic elbow with an adjustable counterbalance mechanism to counteract the mass of terminal devices such as arms and hands at varying angular positions.

BACKGROUND OF THE INVENTION

Prosthetic elbows typically include a forearm and a fixed member structure that is configured to connect to an upper arm portion. The forearm member may be flexed either directly or by mechanical connection via harness to the person's body. An end effector is typically added to the end of the forearm to grasp objects. A counterbalance mechanism may be incorporated into the prosthetic elbow to counter act the weight of the forearm and end effector. Existing designs typically incorporate the counterbalance mechanism in the forearm of the prosthetic elbow and therefore the center of mass is located more distal in the prosthetic elbow.

SUMMARY OF THE INVENTION

The present invention provides embodiments of a prosthetic elbow with an adjustable counterbalance mechanism.

In one embodiment, the prosthetic elbow includes a fixed member structure configured to connect to an upper arm portion, a housing structure configured to connect to a forearm portion and a counterbalance mechanism for counterbalancing a weight of the forearm portion. The housing structure may be a cylindrical shape rotatable about an axis of rotation of the cylindrical shape. The axis of rotation of the cylindrical shape coincides with an axis of rotation of the forearm portion, or an axis of rotation of the elbow joint. The housing structure is rotatable relative to the fixed member structure about the axis of rotation of the forearm portion such that the forearm portion is rotatable relative to the upper arm portion.

The counterbalance mechanism is disposed within and supported by the housing structure. In one embodiment, the counterbalance mechanism includes a torsional spring disposed in the housing structure coaxially to the axis of rotation of housing structure. The spring includes a first portion and a second portion rotationally biased relative to the first portion about an axis of the spring. The axis of the spring generally coincides with the axis of rotation of housing structure, or the axis of rotation of the forearm portion.

The spring is attached at a first end to the housing structure. The first end is adjacent to the first portion. In one embodiment, the spring is attached to the fixed member structure at an inner end of the spring. The inner end is adjacent to the second portion. As the housing structure rotates, the outer end of the spring rotates with it, thereby changing the bias of the spring.

In another embodiment, the counterbalance mechanism may further include a cord and pulley arrangement. According to one embodiment of the present invention, the cord and pulley arrangement includes a first pulley, a second pulley and a link member.

The second pulley is mounted to the housing structure such that the second pulley is configured to rotate with the housing structure about the axis of rotation of the elbow joint. The second pulley is also configured to rotate about a second axis of rotation parallel to and offset from the axis of rotation of the elbow joint. The second axis coincides with an axis of the second pulley. The second pulley is connected to the first pulley by a first cord and connected to the link member by a second cord. The first pulley is attached to the second portion of the spring at or adjacent to the inner end of the spring. The link member is fixed to the fixed member structure.

As the forearm rotates, the second pulley rotates with the housing structure and changes the bias of the spring via the outer end of the spring. The second pulley transfers the spring force through the first pulley to the inner end of the spring. The tension at the inner end and outer end of the spring adjust at the same time when the forearm rotates, thereby changing the bias of the spring.

The second cord attached to the second pulley is configured to be offset from the axis of the spring, thereby providing a moment of force, i.e., a torque to act on the forearm.

With the combination of adjusted spring force and the change of the moment arm of the second pulley from the axis of the spring, the cord and pulley system is thus configured to counteract the torque of a forearm due to gravity as the angle of the forearm portion changes relative to the upper arm portion. The adjustment of the spring force depends on the ratio of the radii of the first pulley and the second pulley and the angle of the rotation of the forearm.

The torsional spring may be spirally wound. The torsional spring may be spirally wound, helically wound, or torsion bar type. The prosthetic elbow may further include a spring housing rotatably disposed in the housing structure for housing the spring.

The second cord may be a separate cord from the first cord or may be a continuation of the first cord.

The second pulley may have a radius smaller than or the same as a radius of the first pulley. The spring may be preloaded to counteract the weight of the forearm and the elbow joint.

The prosthetic elbow may further include an adjustment knob for adjusting the preloaded force of the spring.

The prosthetic elbow may further include a gear reduction wheel connecting the adjustment knob to the spring.

The prosthetic elbow may further include a brake for preventing back-drive of the spring.

DETAILED DESCRIPTION OF THE INVENTION

The counterbalance mechanism disclosed herein is a spring actuated mechanism to counteract the mass of a lever arm at varying angular positions. According to an embodiment of the present invention, the moment force of the lever arm is counteracted by an opposite moment force applied by a spring via a cord and pulley arrangement. As the moment force due to gravity changes with the angle change of the lever arm, the opposing moment force applied by the spring due to the cord and pulley arrangement also changes, counteracting the moment force of the lever arm.

Figure 1:
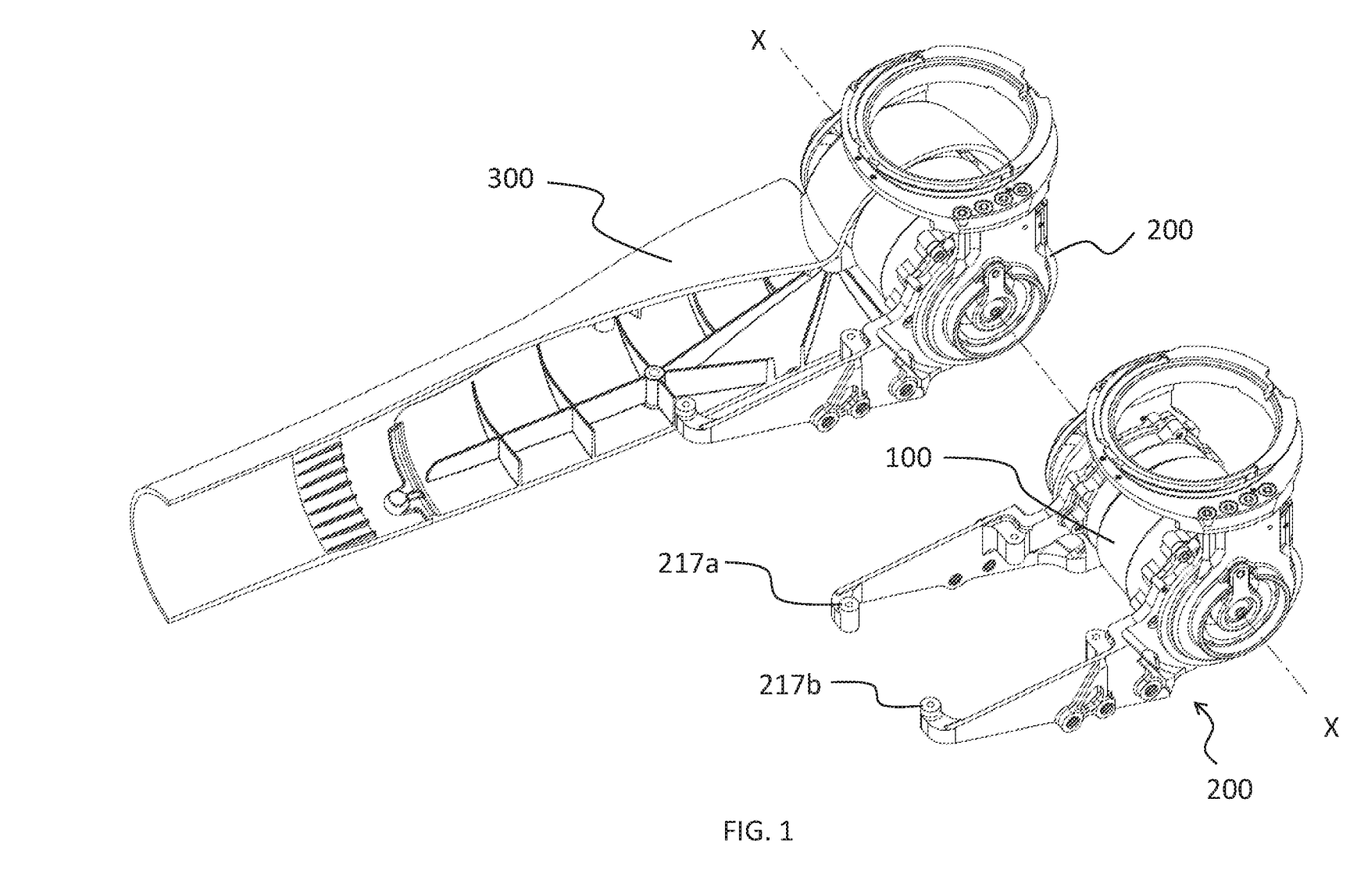
FIG. 1 is a perspective view showing a standing-alone prosthetic elbow as well as a prosthetic elbow attached to a level arm member having a counter balance mechanism in accordance with an embodiment of the present invention.

FIG. 1 illustrates a prosthetic elbow joint 200. The elbow joint may be connected to a lower portion and an upper portion (not shown in FIG. 1). The elbow joint is a pivot joint between the upper portion and lower portion. The upper portion may be referred to as an upper arm portion as it connects to a user's upper arm or upper arm prosthetic. The lower portion may be referred to as a lever arm member or a forearm portion 300. The forearm portion 300 may rotate about an axis x-x of the elbow joint relative to the upper arm portion when the forearm bends or extends.

Without a counterbalance mechanism, under the influence of the gravity, the weight of the lever arm member 300 will pull the lever arm member itself down so that the prosthetic elbow will not be able to hold the lever arm member up. By utilizing a counterbalance mechanism, the user of the prosthetic elbow will be able to hold up the forearm portion so that the forearm portion does not always fall downward under its own weight. The counterbalance mechanism may be a spring-based mechanism. However, when the lever arm member pivots about the elbow joint, the moment force, i.e., the torque, which is acted on the lever arm member will change as the angle of the lever arm member changes relative to the upper arm portion. For a spring-based counterbalance mechanism, the spring bias will increase as the forearm pivots about the elbow joint from a bent orientation to a straight orientation. The spring force may be biased at the greatest when the forearm is down in a straight orientation relative to the upper arm portion and at the lowest when the forearm is bent up in a bent orientation relative to the upper arm portion. When the forearm is perpendicular to the upper arm, the spring force is between the lowest and the greatest. However, the torque on the elbow joint is at its greatest when the forearm is perpendicular to the upper arm since the distance of the center of the mass of the forearm from the pivot axis of the elbow joint is at the greatest at this time.

The present invention provides embodiments of a spring-based counterbalance mechanism which is adapted to the rotation angle of the forearm relative to the upper arm.

Figure 2:
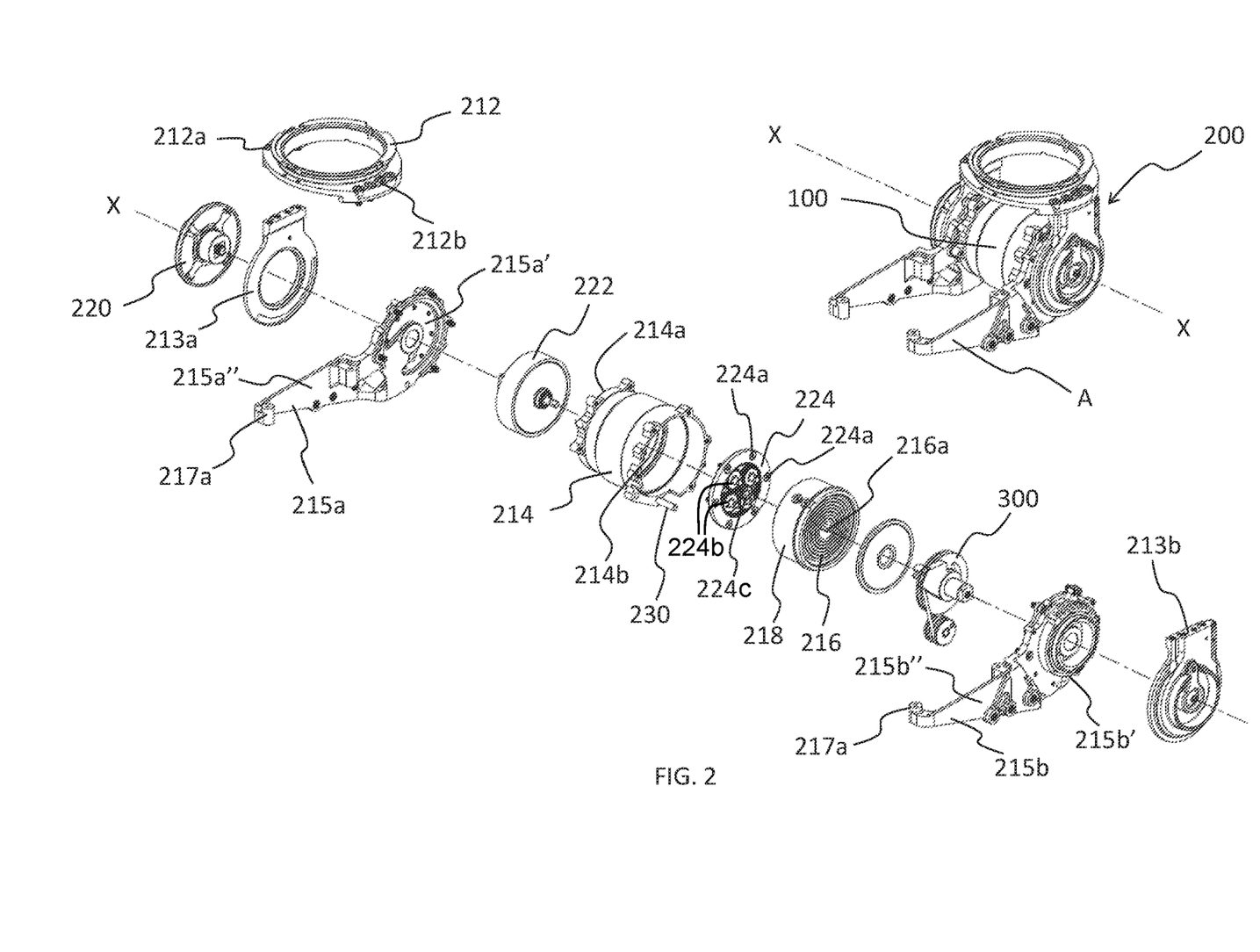
FIG. 2 is a perspective view showing an exploded as well as an assembled prosthetic elbow in a perpendicular orientation having a counterbalance mechanism in accordance with an embodiment of the present invention.

FIG. 2 illustrates an exploded view of a prosthetic elbow showing the components of a counterbalance mechanism in accordance with an embodiment of the present invention. In this embodiment, the prosthetic elbow joint 200 includes the fixed members 212, 213a and 213b. The fixed member 212 is a socket configured to be connected to an upper arm portion (not shown). A pair of substantially parallel fixed members 213a, 213b are connected to two sides 212a, 212b of the fixed member 212 by fasteners such as screws and both are perpendicular to the fixed member 212. The fixed member 212 and the pair of the fixed members 213a, 213b are mounted together forming a fixed structure for containing and supporting the counterbalance mechanism 100.

The elbow joint 200 includes a housing structure for supporting the counterbalance mechanism 100. The housing structure has a cylindrical housing structure member 214 and two housing structure side members 215a, 215b. The cylindrical housing structure member 214 is disposed about an axis x-x. The two housing structure side members 215a, 215b are substantially parallel to each other and extend outwardly perpendicular to the axis x-x. The housing structure side members 215a, 215b each have a circular portion 215a', 215b' extending to an elongated arm portion 215a", 215b". The circular portion 215a', 215b' each are mounted to one of the two sides 214a, 214b of the cylindrical housing structure member 214 by fasteners such as screws. When the circular portions 215a', 215b' of the housing structure side members 215a, 215b are attached to the cylindrical housing structure member 214, the housing structure side members 215a, 215b and the cylindrical housing structure member 214 forms a housing structure capable of rotating about the axis x-x within the fixed member structure. The elongated arm portions 215a", 215b" are configured to be attached to the forearm portion 300 at the ends 217a, 217b of the elongated arm portions 215a", 215b" such that when the forearm portion bends or extends relative to the upper arm portion about the elbow joint axis x-x, the housing structure rotates about the axis x-x with the forearm portion.

The counterbalance mechanism 100 includes a torsion spring 216 disposed within and supported by a spring housing 218. The torsion spring 216 may be spirally wounded with its outer end attached to the spring housing 218 and is located coaxial to the axis x-x of rotation of the forearm. As the spring housing rotates, the outer end of the spring rotates with it, thereby changing the bias of the spring.

A planetary gear reduction wheel 224 may be attached to a side of the spring housing at various planet gears 224b such that the spring housing rotates as the gear reduction wheel rotates. The ring gear 224a is attached to the housing structure. An adjustment knob 220 may be provided and configured to connect to the center 224c of the gear reduction wheel 224 and acts to rotate the spring housing, relative to the housing structure member 214, through the gear reduction wheel 224 which reduces the amount of effort needed to adjust the tension on the spring and to allow more precise adjustment. A brake mechanism 222 may be provided between the adjustment knob 220 and the gear reduction 224 to hold the spring from rotating after adjustment. The spring housing is configured to rotate relative to the housing structure so that the spring tension can be adjusted by the adjustment knob 220. When the adjustment knob is fixed, the spring housing can no longer rotate relative to the housing structure, e.g., when the forearm changes the angle relative to the upper arm. In other words, the spring housing will move with the housing structure.

In the application of an upper limb prosthetic device, the coaxially adjustable counterbalance mechanism locates the majority of its mass at the axis of rotation of the elbow joint, therefore allowing the center of mass of the prosthetic device to be located more proximal to the elbow joint. By locating the center of mass of the prosthetic as proximal as possible to the elbow joint, the prosthetic device places less of a moment force on the residual limb, resulting in the prosthetics typically feeling more comfortable to the end user and being perceivably lighter than having a more distal mass.

In an embodiment of the present invention, as shown in FIGS. 2-7, the counterbalance mechanism may further include a cord and pulley arrangement 300. As illustrated in an exploded view in FIG. 5, the cord and pulley arrangement includes three main parts: a first pulley 302, a fixed link member 306 and a second pulley 304. The first pulley 302 is attached to an inner end 216a of the spring 216 through the center piece 312 of the first pulley 302. The first pulley 302 has one groove for a first cord 308. The first cord 308 partially wraps around the first pulley 302 at one end and partially around a first groove 316 of the second pulley 304 at the other end. The first pulley transfers spring force through the first cord 308 between the first pulley 302 and the second pulley 304. The second pulley 304 has an aperture 320 at the center of its body. The aperture engages with a knob 230 on the housing structure member 214 such that the second pulley is mounted on the housing structure. The second pulley is also attached to the fixed link member 306 through a second cord 310. The second cord 310 partially wraps around a second groove 318 of the second pulley 304. The fixed link member 306 is connected to the first pulley 302, but is attached to the fixed member 213b. When the forearm bends or extends, the fixed link member 306, along with the fixed member 213b, do not move relative to the upper arm portion. The second pulley may be the same size or smaller size than the first pulley. Due to the space constraint, the second pulley is preferred to be smaller than the first pulley. The first cord and second cord are not elastic. In another embodiment, the second cord may be the continuation of the first cord.

Figure 5:
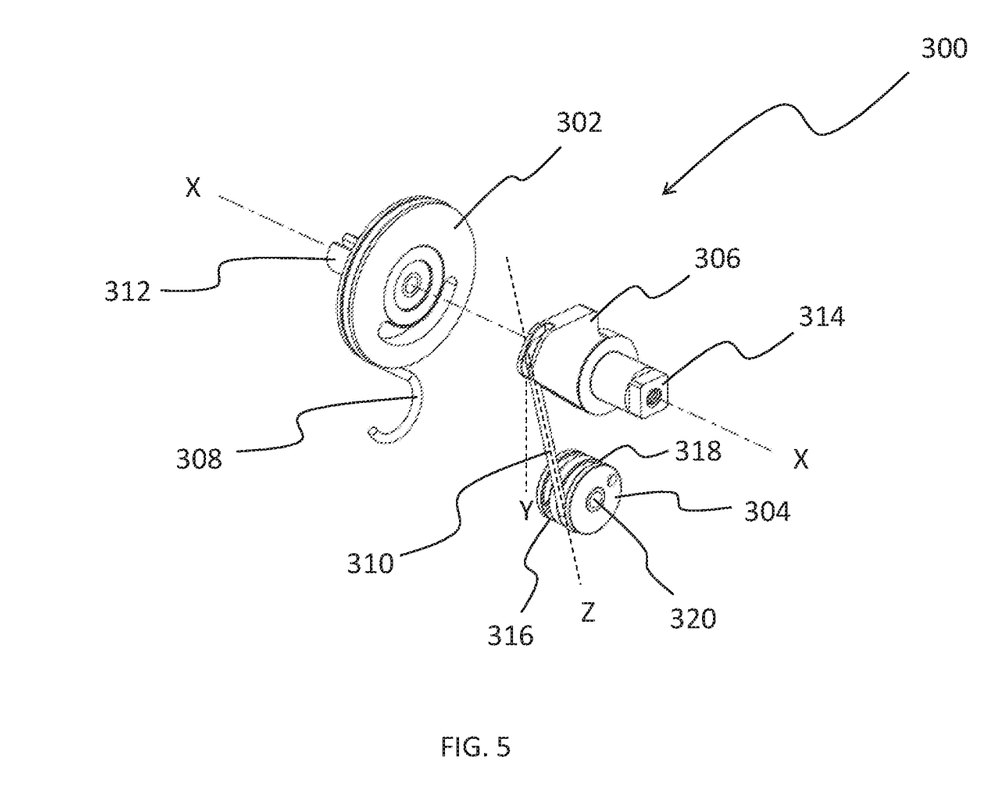
FIG. 5 is a perspective view showing an exploded cord and pulley mechanism which is a part of the counterbalance mechanism in a perpendicular orientation in accordance with an embodiment of the present invention.

Based on the configuration above-described, the first pulley 302 is coupled to the inner end 216a of the spring at the center piece 312 of the first pulley, the second pulley 304 is attached to the housing structure and therefore moves with the housing structure as the outer end of the spring moves with the housing structure, and the first pulley is coupled to the second pulley via the first cord. Therefore, the spring force acts on the first pulley and then on the second pulley through the first pulley. In return, as the second pulley moves relative to the fixed member, the changing positions of the second pulley causes a change in the pull angle between the second pulley and the fixed member and therefore, changes the reacting force applied to the first pulley and then to the spring through the first pulley.

Figure 7:
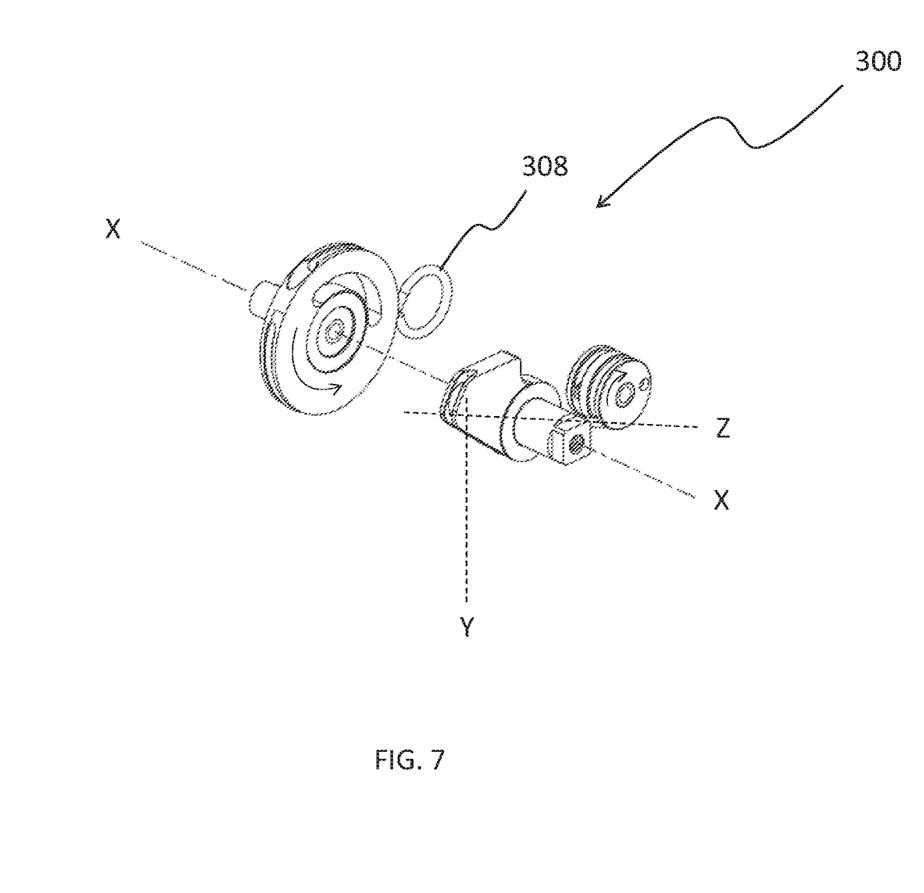
FIG. 7 is a perspective view showing an exploded cord and pulley mechanism which is a part of the counterbalance mechanism in a straight orientation in accordance with an embodiment of the present invention.
Figure 8:
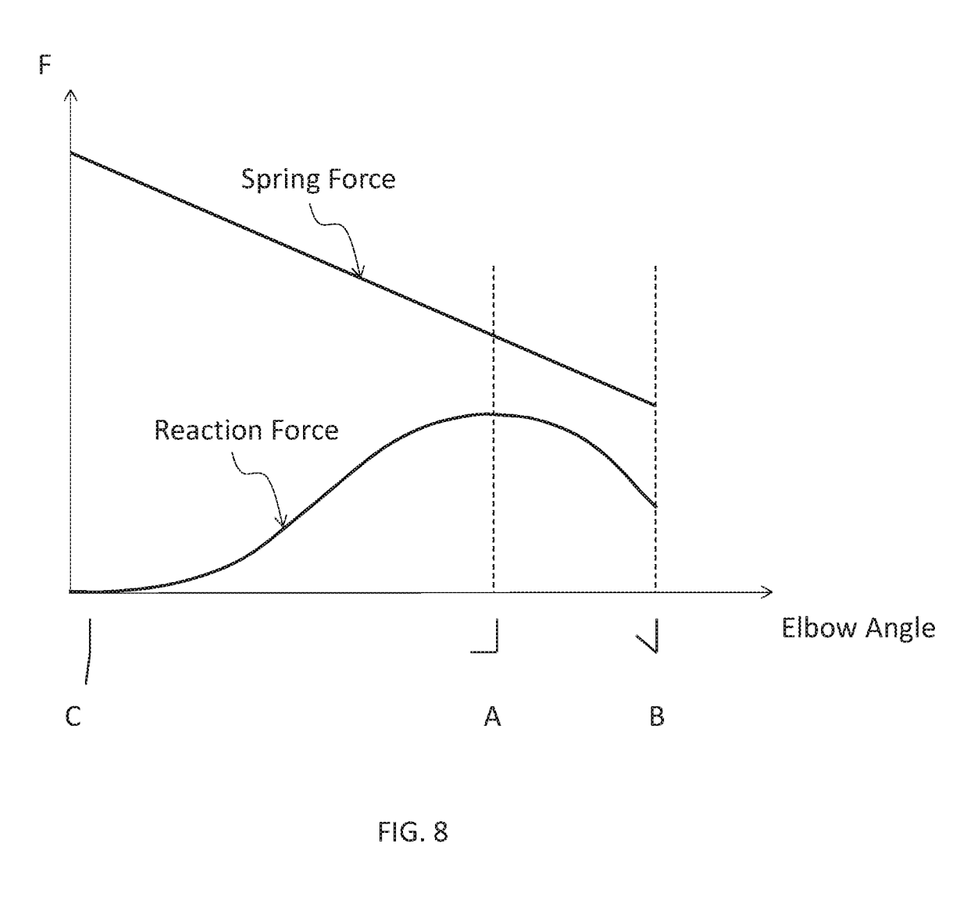
FIG. 8 is a graph illustrating the spring force profile as the forearm flexes or extends.

When the forearm is in a perpendicular orientation relative to the upper arm portion, the configuration of the elbow joint 200 and cord and pulley arrangement 300 are as shown in FIGS. 2 and 5. The second pulley 304 is directly below the fixed link member 306. The force acting on the forearm is at the greatest, corresponding to the torque of the forearm in this orientation. The spring force is not necessarily the greatest, as shown in FIG. 8, but the resulting force acting to lift the housing structure which is attached to the forearm member is greatest with the elbow at approximately 90 degrees due to the angle of pull between the second pulley 304 and the fixed member 306. The cord 310 is offset with respect to the x-x axis. The greater distance between the x-x axis and the Z axis of cord 310 results in a larger moment arm length between the two axes. For example, when the elbow is straightened, the Z axis of cord 310 intersects axis x-x, as shown in FIG. 7, so the moment arm length is 0. Even though the spring is actually deflected the most when the elbow is straight, and the tension on the cords is the greatest at this configuration (configuration C), as shown in FIG. 8, the resulting force pulling up on the forearm is 0. As the elbow is bent, the spring force and therefore tension in the cords decreases, but the increase in moment arm length i.e. distance between x-x axis and Z axis of the cord 310, counters the reducing spring force, and actually results in increasing the force acting on the housing structure, which is in turn attached to the forearm member.

Figure 3:
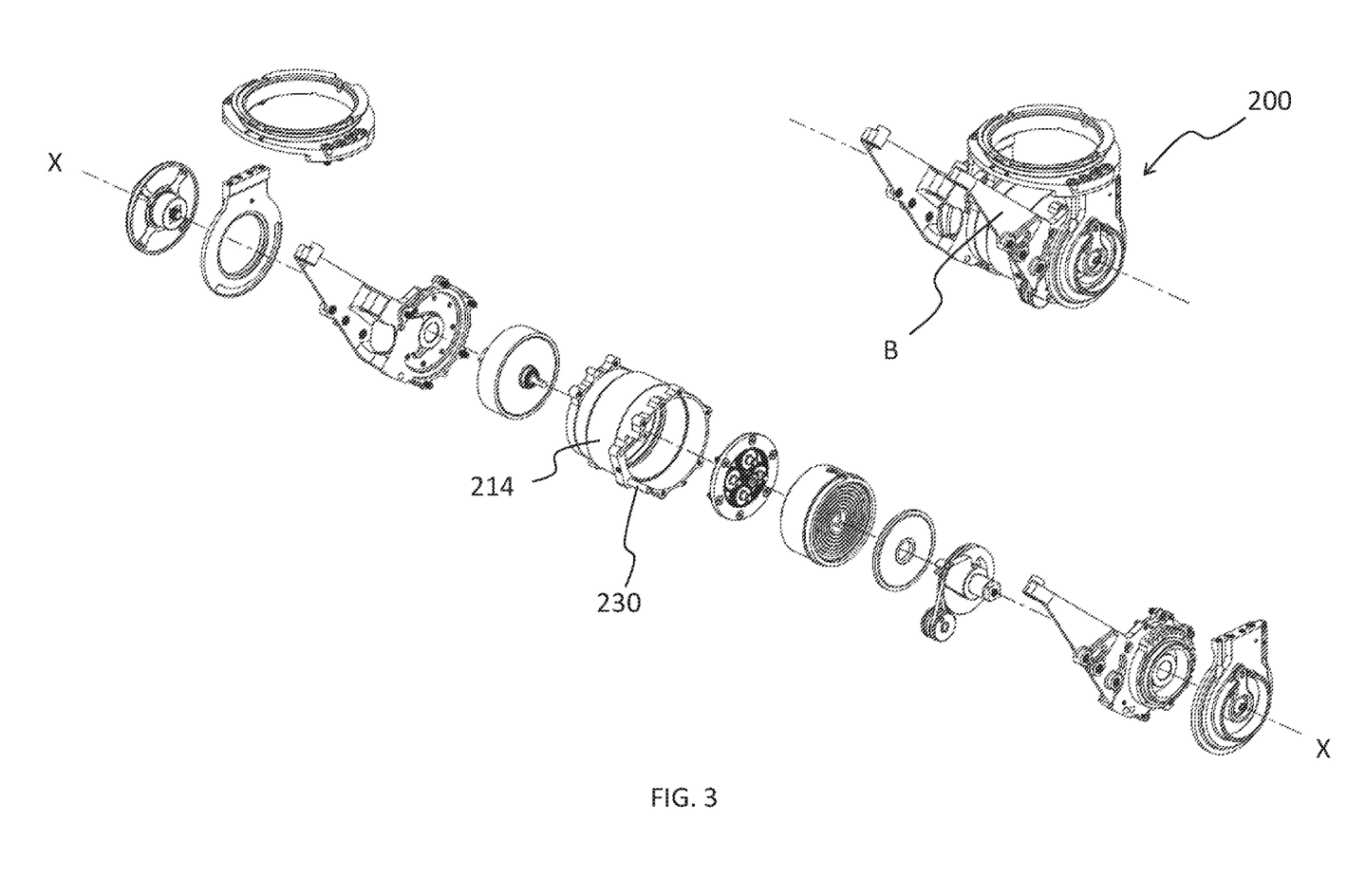
FIG. 3 is a perspective view showing an exploded as well as an assembled prosthetic elbow in a bent orientation having a counterbalance mechanism in accordance with an embodiment of the present invention.
Figure 6:
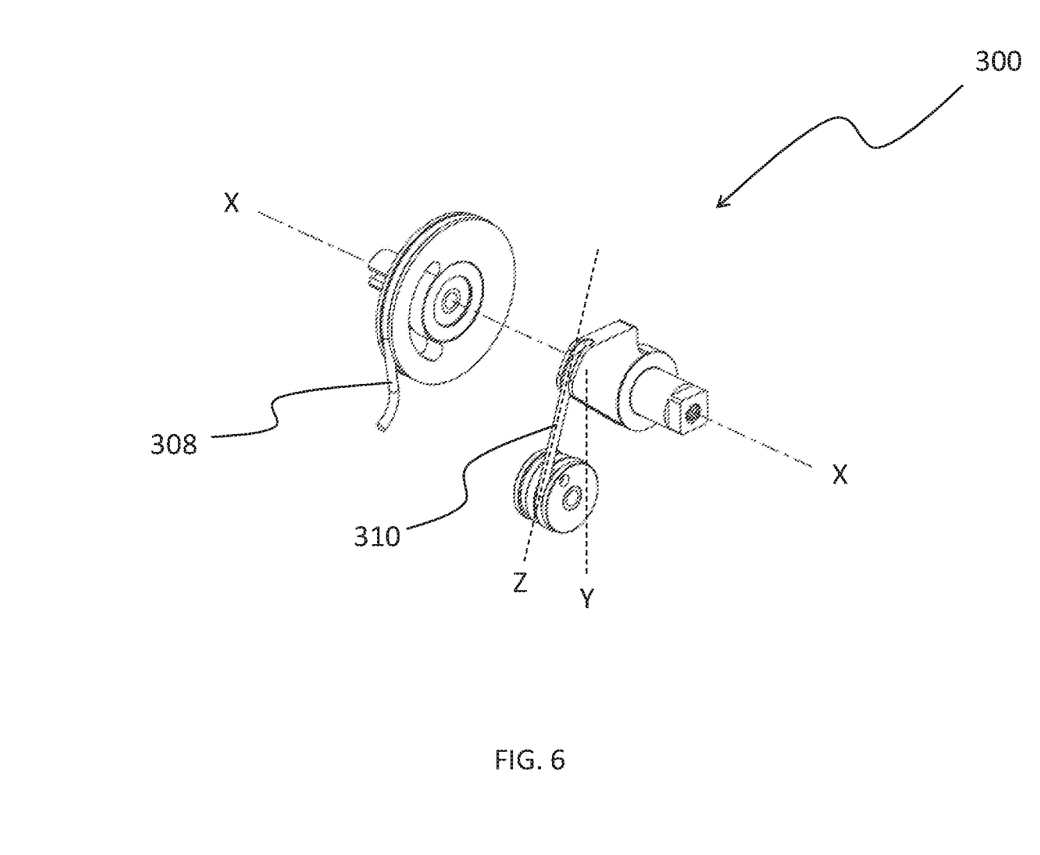
FIG. 6 is a perspective view showing an exploded cord and pulley mechanism which is a part of the counterbalance mechanism in a bent orientation in accordance with an embodiment of the present invention.

When the forearm is in the bent orientation relative to the upper arm portion, the configuration of the elbow joint 200 and the cord and pulley arrangement 300 are as shown in FIGS. 3 and 6. The elongated arm portions 215a", 215b" of the housing structure rotate clockwise and move upwards with the forearm. As the housing structure rotates clockwise due to the rotation of the forearm, the second pulley 304 mounted on the knob 230 moves up and to the left relative to its position below the fixed link member 306 in the perpendicular orientation. As shown in FIG. 6, the second cord 310 is positioned at an angle and to the left relative to the vertical direction Y. Under the tension of the spring, the first pulley is biased to spin clockwise and therefore pulls on the first cord 308 to cause the second pulley 304 to spin counterclockwise such that the second cord continues to tightly engage with the second pulley. As the housing structure 214 rotates clockwise, the outer end of the spring 126 also moves with the spring housing 218 within the housing structure. The combination of the rotation of the outer end of the spring and the change of the reaction force applied by the second pulley 304 causes the spring force to decrease relative to the perpendicular orientation and therefore, to counterbalance the changing torque moment of the forearm.

Figure 4:
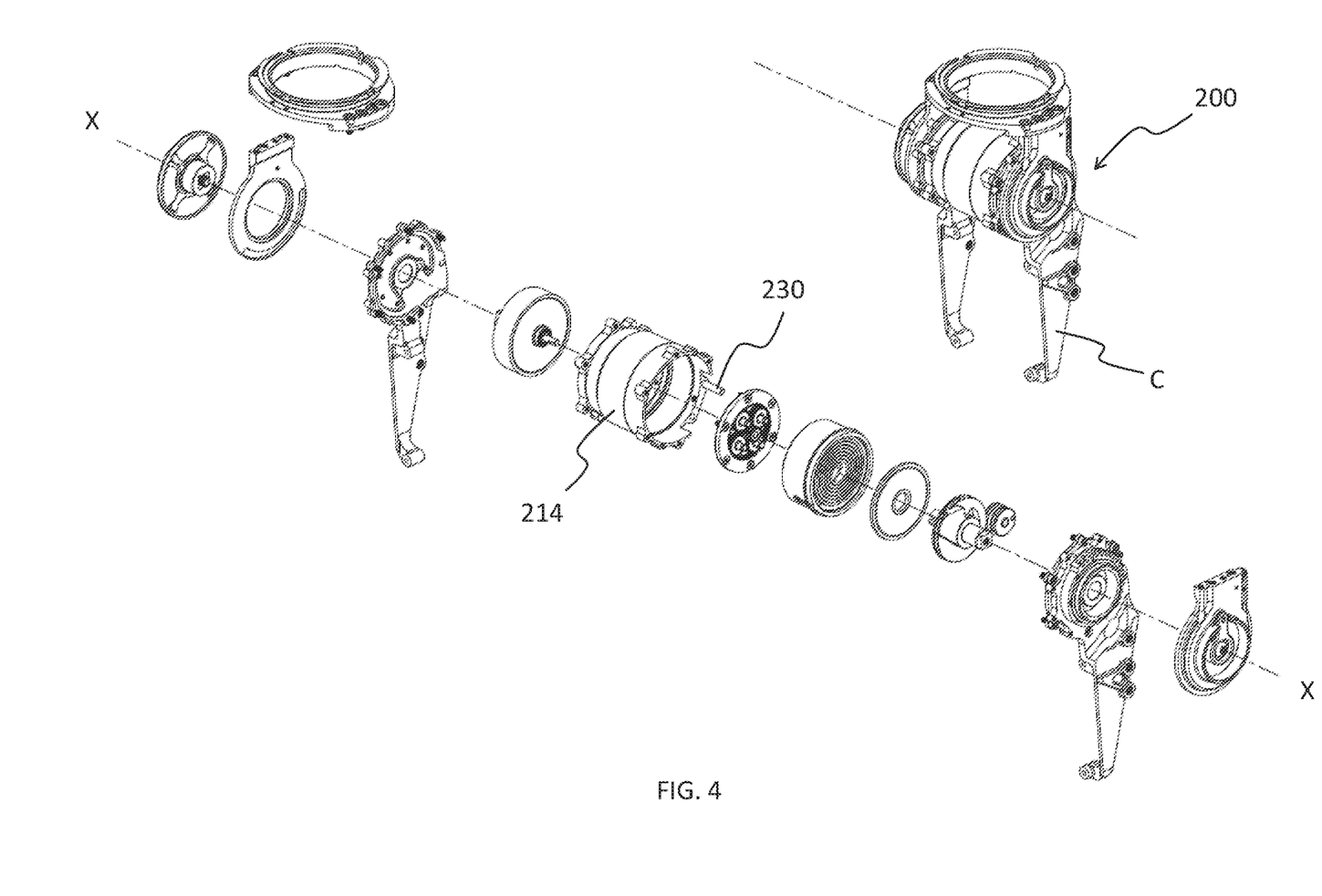
FIG. 4 is a perspective view showing an exploded as well as an assembled prosthetic elbow in a straight orientation having a counterbalance mechanism in accordance with an embodiment of the present invention.

When the forearm is in an extended orientation, as indicated as C in FIG. 4 and also shown in FIG. 7, the housing structure 214 rotates counterclockwise such that the knob 230 and hence the second pulley 304 rotates counterclockwise and moves to the right of the x-x axis. The first cord 308 is also pulled to the right of the first pulley and at an angle almost perpendicular to the y direction and causes the first pulley to be biased to rotate counterclockwise to adjust the inner end of the spring therefore changing the spring tension. Thus, the rotation of the forearm causes the housing structure to rotate. The rotation of the housing structure causes the second pulley 304 to rotate. The rotation of the second pulley 304 causes the first pulley 302 to be biased to rotate and therefore causes the inner end of the spring to adjust the tension. Through this mechanism, the adjustment of the outer end of the spring is relayed to the inner end of the spring through the cord and pulley arrangement. The inner end of the spring and the outer end of the spring adjust at a different pace. The ratio is the same as the ratio of the second pulley radius to the first pulley radius.

FIG. 8 illustrates the profile of the spring force and the reaction force as the forearm bends or extends. The spring can be preloaded. The preloaded spring force can be adjusted using the adjustment knob. The preloaded spring force stays constant without any movement of the forearm. The turning of the adjustment knob will change the preloaded spring force, and the preloaded spring force will remain at that level without any movement of the forearm. The configuration A corresponds to the forearm in a perpendicular orientation, as indicated in FIG. 2. The configuration B corresponds to the forearm in a bent orientation, as indicated in FIG. 3. The configuration C corresponds to the forearm in an extended orientation, as indicated in FIG. 4. The reaction force acting to lift the housing structure is at the greatest at configuration A when the forearm is in a perpendicular orientation, counterbalancing the torque moment in this orientation, which is the greatest among all the orientations. The reaction force adjusts lower corresponding to the configurations B and C to counterbalance the lower torque moments in these orientations.

As will be clear to those of skill in the art, the embodiments of the present invention illustrated and discussed herein may be altered in various ways without departing from the scope or teaching of the present invention. Also, elements and aspects of one embodiment may be combined with elements and aspects of another embodiment. It is the following claims, including all equivalents, which define the scope of the invention.

The invention claimed is:

1. A prosthetic elbow with an adjustable counterbalance mechanism, comprising:
    a fixed member structure configured to connect to an upper arm portion;
    a housing structure configured to connect to a forearm portion, the housing structure rotatable relative to the fixed member structure about an axis of rotation of the forearm portion;
    a counterbalance mechanism for counterbalancing a weight of the forearm portion, the counterbalance mechanism disposed within and supported by the housing structure, the counterbalance mechanism comprising:
        a torsional spring disposed in the housing structure coaxially to the axis of rotation of the forearm portion, the spring having a first portion and a second portion rotationally biased relative to the first portion, the spring attached at a first end to the housing structure;
        a cord and pulley arrangement including a first pulley, a link member and a second pulley, the first pulley attached to a second portion of the spring, the first pulley connected to the second pulley by a first cord, the link member fixed to the fixed member structure, the second pulley pivotally attached to the housing structure and connected to the link member by a second cord;
        the second pulley being configured to rotate with the housing structure about the axis of rotation of the forearm portion and rotate about a second axis of rotation parallel to and offset from the axis of rotation of the forearm portion;
    wherein the cord and pulley arrangement is configured to transfer a moment of force due to spring force to the housing structure thereby to the forearm portion, the cord and pulley system being configured to adjust the transferred moment of force to counteract a torque of a forearm due to gravity as the angle of the forearm portion changes relative to the upper arm portion.

2. The prosthetic elbow of claim 1, wherein the torsional spring is spirally wound.

3. The prosthetic elbow of claim 1, further comprising a spring housing for housing the spring, the spring housing rotatably disposed in the housing structure.

4. The prosthetic elbow of claim 1, wherein the second cord is a continuation of the first cord.

5. The prosthetic elbow of claim 1, wherein the second pulley has a radius smaller than a radius of the first pulley.

6. The prosthetic elbow of claim 1, wherein the spring is preloaded.

7. The prosthetic elbow of claim 6, further comprising an adjustment knob for adjusting the preloaded force of the spring.

8. The prosthetic elbow of claim 7, further comprising a gear reduction wheel connecting the adjustment knob to the spring.

9. The prosthetic elbow of claim 1, further comprising a brake for preventing back-drive of the spring.

10. The prosthetic elbow of claim 1, wherein a distance between an axis along the second cord and the axis of the rotation is adjustable as the second pulley moves.

* * * * *